United States Patent [19]

Orlando

[11] Patent Number: 4,738,264

[45] Date of Patent: * Apr. 19, 1988

[54] HEART AND BREATHING ALARM MONITOR

[76] Inventor: Carl Orlando, 47 Willow Rd., Tinton Falls, N.J. 07724

[*] Notice: The portion of the term of this patent subsequent to Apr. 14, 2004 has been disclaimed.

[21] Appl. No.: 930,228

[22] Filed: Nov. 13, 1986

Related U.S. Application Data

[63] Continuation of Ser. No. 715,591, Mar. 25, 1985, Pat. No. 4,657,025.

[51] Int. Cl.$^4$ .................. A61B 5/02; A61B 5/08
[52] U.S. Cl. .................. 128/671; 128/714; 128/721; 73/654
[58] Field of Search .............. 128/670, 671, 716, 721, 128/722, 714, 773

[56] References Cited

U.S. PATENT DOCUMENTS

| | | | |
|---|---|---|---|
| 1,686,504 | 10/1928 | Dodge et al. | 128/773 |
| 2,702,883 | 2/1955 | Petroff et al. | 128/687 |
| 2,740,946 | 4/1956 | Geneslay et al. | 73/654 |
| 3,325,799 | 6/1967 | Farris | 128/721 |
| 4,066,072 | 1/1978 | Cummins | 128/716 |
| 4,138,893 | 2/1979 | Holmes et al. | 73/654 |
| 4,494,553 | 1/1985 | Sciarra et al. | 128/671 |

OTHER PUBLICATIONS

Wilbarger et al., American J. Med. Elec., Jul.-Sep. 1964, pp. 199-200.

Turner, J. Mt. Sinai Hosp. of NY, Mar.-Apr. 1951, p. 1060.

*Primary Examiner*—Kyle L. Howell
*Assistant Examiner*—John C. Hanley
*Attorney, Agent, or Firm*—Darby & Darby

[57] ABSTRACT

A device for sensing heart and breathing rates in a single transducer and having electronic and filtering circuits to process the electrical signal generated by the transducer. The transducer is an electromagnetic sensor constructed to enhance sensitivity in the vertical direction of vibration produced on a conventional bed by the action of patient's heart beat and breathing functions and achieves sufficient sensitivity with no physical coupling between the patient resting in bed and the sensor placed on the bed away from the patient. The electronic circuits integrates the electrical energy generated by the sensor that pertains to cardiac and breathing information and sets off an alarm when pre-set circuits of these functions have been surpassed. The device has applications in monitoring SID Syndrome and non-ambulatory patients.

5 Claims, 2 Drawing Sheets

HEART AND BREATHING ALARM MONITOR

The present application is a continuation of co-pending patent application Ser. No. 715,591, filed Mar. 25, 1985, now U.S. Pat. No. 4,657,025.

BACKGROUND OF THE INVENTION

This invention relates to an instrument for generating an alarm when a resting patient's heart rate or respiratory rate varies from previously established values. This device is useful in monitoring patients with fluctuating heart and respiratory rates which may be indicative of potential life threatening emergencies, such as Sudden Infant Death Syndrome (SIDS), nocturnal apnea, suffocation, and certaian diseases of the heart which causes rapid or diminished cardiac rates.

Present instruments used to monitor apnea and bradycardia rely on two separate sensors that attach physically to the patient. These devices restrict the patient's movements, and are very uncomfortable especially when used on neonatal infants. In addition, the complexity of obtaining positive mechanical probes attached to the patient and the electrical connections required. Make the use of these sensors cumbersome and ineffective due to the danger of separation of the probes from the patient. The complexity of these instruments also requires professional operators for best results to operate the device.

In a previous patent application, Ser. No. 129,588, I have described a device that is non-invasive and is placed on any part of a conventional bed or crib where the patient rests to monitor the heart and breathing functions. The present invention describes a single sensor which is sensitive to both the heart beat and breathing functions. An improved electronic circuit has been achieved which takes advantage of the dual sensor capabilities to detect deviations of these functions. The electronic circuit is capable of producing an alarm when a deviation from present limits occurs.

SUMMARY OF THE INVENTION

Available electronic heart and breathing monitors employ two separate transducers to obtain data, one for the heart and one for the breathing functions. These sensors, Re: Harway, Jr. et al., U.S. Pat. No. 4,033,332; Bashman, U.S. Pat. No. 3,898,981, are coupled to the patient by mechanical means. Heart monitors employ electronic probes attached to the patient. Breathing monitors use special mechanical devices to activate the sensors. The monitoring control device produces an alarm when there is a deviation of heart or breathing function different from the norm set by the attending nurse or the operator of the instrument. In many instances, in the presently available devices, a signal processing circuit converts the signal produced by the sensors in a format manageable by the operator and compatible with the overall electrical circuit of the device. In monitoring the heart signal, for example, the circuit is designed to detect the heart beat rate and uses this digital data to activate an electronic counter which is sensitive to a time period. When a deviation of the heart beat rate varies from a predetermined value, the circuit that senses the rate, triggers an alarm signal. The sensor for detecting and monitoring breathing employs a similar circuit. These techniques are very useful for obtaining certain diagnostic data of cardiac functions and the breathing mechanism. In my invention, however, the diagnostic application is not of primary consideration except for detecting SIDS. My invention is concerned with monitoring deviations of these functions from a predetermined norm which may be indicative of the onset of SIDS. For this application, my invention may be fabricated with less sophistication to achieve a more versatile use, resulting in an instrument which is reliable and easily operable by an inexperienced operator.

My invention utilizes a single transducer to detect both the heart beat and breathing rates. These signals are combined electronically and the circuit detects the integrated energy of the two signals. A simple electronic circuit detects deviation of the combined integrated power. A deviation from a normal integrated energy is sensed, and when it is more or less, an alarm signal is generated to alert an attendant. The transducer and associated circuitry for the complete functioning of the device is housed in an apparatus of approximately 16 cubic inches. The apparatus can contain, in addition to the transducer, the electronic battery power supply, a radio transmitter or a direct line to transmit the alarm signal to a remote station. This apparatus is placed on the normal bed or normal crib of the patient without physical coupling to the patient. A small radio receiver can be placed away from the apparatus to receive the alarm signal and produce an audible or visual alarm.

In the application of my invention, where it is necessary to obtain or display individual data of only the heart beat rate, or the breathing rate, the apparatus provides these outputs. These functions are accomplished by employing electric filtering to separate the two different signals.

The literature teaches that there are transducers available that are able to detect very minute movements of the body produced by the acceleration of the blood as it moves in the circulatory system. Data from these transducers can only be obtained when the body is freely suspended and can move uninterrupted by friction. Cunningham and Danders, Bibliography Cardial, 19, pages 1-6, 1967, constructed a bed-like structure which floated on air bearings to detect the blood movement and obtained ballistocardiogram (BCG) readings of the heart function. The air bearing construction allowed the bed-like structure to be freely suspended and isolated from ambient mechanical movement of the pavement. An accelerometer was used to detect the heart functions.

According to Starr and Nordergroad, American Heart Journal, 64, pages 79–100, 1962, ballistocardiographic techniques require that the mass of the bed be extremely small. The body weight of the patient being observed should be at least ten times greater than the bed on which he lays. Other workers in this field have concluded that if ballistocardiography is used as a non-invasive technique for obtaining heart data, the bed or other structures, such as chairs, tables, or platform used by the patient, must be considered as part of the special equipment required by the system. This limitation has made the use of ballistocardiography expensive and impractical.

The most successful transducers employed in ballistocardiograms have been those used to detect acceleration by means of piezo-resistive techniques. Transducers of this type have a natural frequency range above that which can detect heart beat, about 1.2 Hertz. This characteristic makes their use cumbersome, and require sophisticated electronic circuitry for adopting them for the low frequency necessary to detect heart rates. I have also found that available transducers are not effective to produce a signal of the heart beat in combination with the breathing rate of a patient for monitoring these two functions at the same time. In addition, Re: Starr, in The Harvey Lectures, page 199, delivered January 1947 and Curtis, H. J., The Design of the Ballis tocardiograph, Am J Physiol 142: 1-11, 1944, concluded that breathing functions have a deleterious effect on heart monitoring in ballistocardiography.

In conjunction with the present invention, I have invented a new type of transducer capable of detecting these two functions simultaneously in an efficient manner. The transducer consists of a small cylindrical magnet which is surrounded by an electrical coil so that when the coil is made to move, it produces an electrical current proportional to the movement of the body, and generates a voltage proportional to the frequency of the relative movement between the coil and the magnet assembly. The magnet and associated pole pieces are held fixed to the transducer container or case, which rests on the patient's bed. A thin cylindrical rigid structure is filled with liquid which rests on a flexible liquid seal or membrane which is attached to the coil assembly. The liquid forms an incompressible medium which produces a force on the surface of the movable membrane and hence also on the coil assembly. This transducer, in which the vertical liquid column loads the coil assembly, efficiently senses vertical movement. I have found experimentally that this characteristic is very effective in detecting the body movements caused by the heart beat and breathing, since heart and breathing functions mainly produce vertical movement of the bed and mattress on which a subject lies. This transducer is placed on a conventional bed where the patient lies, attached only by gravity. The transducer can be placed away from the patient for example at rear of the patient's feet. The bed need not be isolated from the floor. Thus the bed is not a component part of the system as it is in the case of ballistocardiogram devices and thus the transducer and its associated circuitry and other types of monitors can be placed on any bed.

DESCRIPTION OF THE PREFERRED EMBODIMENT

Figure 1:
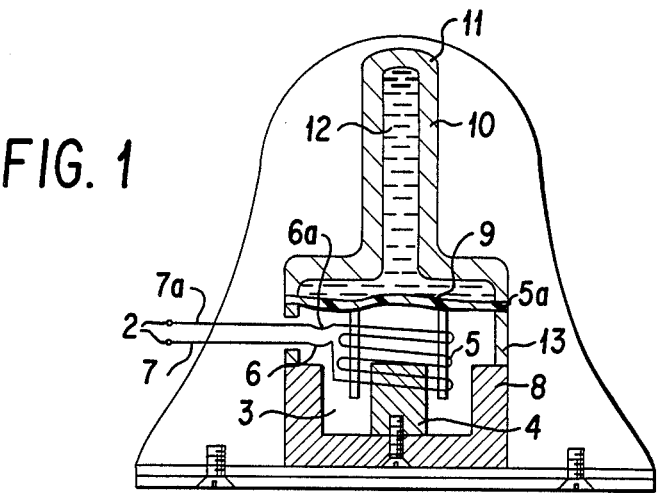
FIG. 1 is a drawing illustrating the novel heart and breathing rate transducer.

FIG. 1 is an illustrative drawing of a Motion Detection Transducer which I have invented to detect the minute movements of a patient lying in a conventional bed. The patient's natural coupling with the mattress where he rests produces a movement throughout the mattress which is sensed by the transducer. The design of the transducer enhances sensitivity in one direction, namely the vertical direction, which is the direction of most of the mattress movement due to heart and respiratory action of a person lying on the mattress. This design allows for an improved signal-to-noise ratio compared to sensors that have omnidirectional sensitivity, as it is evident in Hawley, et al., U.S. Pat. No. 3,270,565.

The physical and mechanical aspects of this sensor may be described as follows: Given a narrow cylindrical column of liquid hermetically enclosed. Let the column stand vertically on a platform freely movable in all three axes. Apply a force on the platform along the vertical axis. This force in turn accelerates the column of liquid in the upward direction. However, since the liquid is enclosed, the upward acceleration creates an increase in pressure at the lower end of the thin column while producing a lower pressure at the top of the column. The pressure produced is proportional to the height of the column and the density of the liquid. The change in pressure produces a force which may be detected by an electromagnetic device. When a force is applied to the platform in the horizontal direction, it creates in turn an acceleration in the thin column of liquid in a sideways direction. The force produced by this action is similar to that obtained by having the force in the vertical direction, except that the pressure produced in the horizontal direction is much less because the configuration of the liquid in the horizontal direction is only the result of the effective diameter of the thin column of liquid. I have found experimentally that the thinner the column is made, the greater is the directional sensitivity in the direction of the column. I also have found experimentally that the sensor I have invented enhances signals produced by the vertical movement of a person resting in bed, and attenuates those signals that are off vertical. Ambient mechanical noises which affect the movement of the bed omnidirectionally are suppressed. Therefore, the resultant signal-to-noise ratio of my sensor is improved.

A better understanding of the construction of the transducer may be obtained by referring to FIG. 1.

The case or container 1, which may be constructed of such material as aluminum, encloses the sensor mechanism and provides terminal electrical connections 2. The sensor mechanism consists of an enclosure 3 which houses a magnet 4 mounted in a magnetic flux conducting pole piece 8. Coil 5 is supported by cylindrical tube 5a which surrounds magnet 4. The cup-shaped pole piece 8 forms part of the magnetic circuit to produce a radial magnetic flux in the air gap in which the coil and its support 5a are mounted, so that the flux lines are cut when the coil and its support move vertically in the air gap. The structure described thus far is similar to the magnetic and voice coil system of a loudspeaker. Flexible elements 6 and 6a are connected to wires 7 and 7a which bring the output electrical signal to terminals 2. Cylindrical tube 5a is attached to flexible membrane 9, which may be constructed of a very thin material such as Mylar having a thickness of about 0.001 inches. Membrane 9 centers coil 5 around the magnet and prevents contact with the magnet during operation. Membrane 9 also makes a hermetical seal with enclosure 3 and the vertical column 10. Column 10, which can be a hollow tube made of a suitable material such as aluminum, is sealed at the top by a mechanical fixed seal or cap 11. Column 10 is totally filled with liquid 12. The liquid employed may be water, aqueous solutions of salt or increased specific gravity, organic solutions, or other substance such as mercury, which is more efficient because of its higher specific gravity. Cylindrical tube 13 is attached to the top of pole piece 8, which in turn is attached to membrane 9 and column 10 to produce a rigid assembly. The attaching medium may consist of a suitable cement such as an epoxy compound. Tube 5a is attached to membrane 9 using the same type cement.

During the operation of my motion detector transducer, the device is placed on a conventional mattress, which may be covered by a conventional sheet or blanket, where a patient is resting. The patient's heart and breathing functions create a rhythmic movement on the mattress. The mattress movement produces a force in liquid 12 perpendicular to the surface of the mattress. The force of the liquid is transmitted through the rigid column 10 and reacts with the flexible membrane 9, which in turn creates a movement of coil 5 resulting in the generation of a current which is proportionate to the amplitude of the movement of the mattress and exhibits the same frequency as the combined frequencies of the heart and breathing functions. The current generated by the transducer is fed to an electronic circuit for processing.

An alternate explanation of the mode of operation is that the weight of the liquid column resting on the movable coil assembly represents a mass loading of the system which lowers the natural resonant frequency thereof to the vicinity of the frequency of the signals of interest. These frequencies are approximately 1-2 Hz for heart signals and approximately 0.3 Hz for respiration signals.

Also the mass loading of the moving coil tends to hold the coil stationary if the case 1 is moved by an external force such as the aforementioned body functions. The resultant relative movement between the magnet assembly and the coil assembly will produce an output signal at terminals 2.

Figure 2:
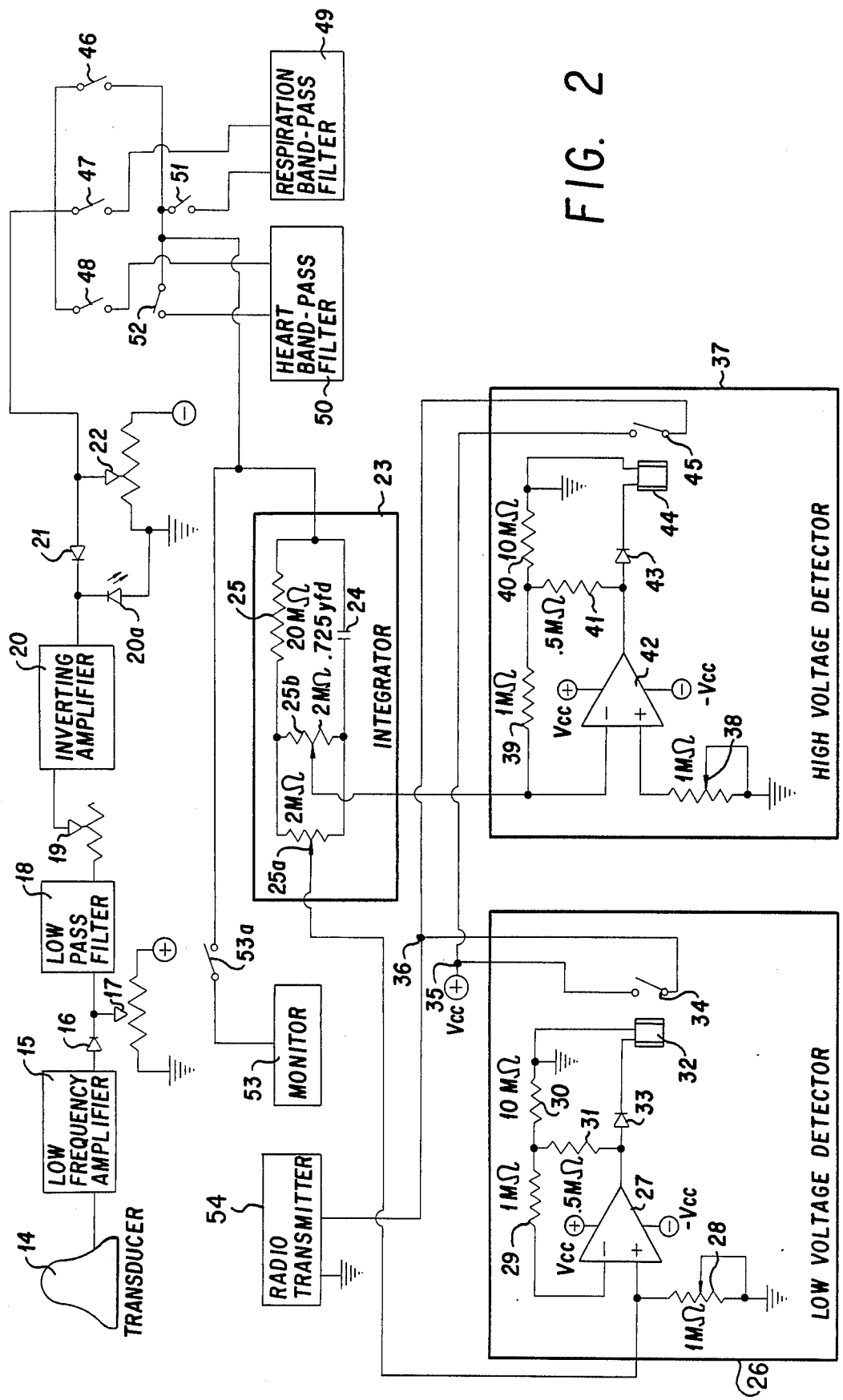
FIG. 2 is a schematic diagram of the novel electronic circuitry of the invention used to amplify and process the electrical signal produced by the heart and breathing rate transducer to obtain an alarm signal.

Turning to FIG. 2, which is an electrical schematic diagram of the invention, motion detection transducer 14 is connected to a low frequency amplifier 15 to amplify the A.C. voltage signal produced by transducer 14 when monitoring a patient. Diode 16 rectifies the signal so that only the positive element is reproduced. Bias network 17 supplies a positive bias voltage to the anode of diode 16 such that very low D.C. signals are blocked. The bias network 17 thus acts as an adjustable threshold regulator to block low amplitudes caused by ambient noises which may be picked up by the transducer 14. The output of diode 16 is fed to a low pass filter 18 which allows only frequencies of about 4 Hertz or less pass and cuts off frequencies much above 4 Hertz. Attenuator 19 is used as a sensitivity control to set the signal output at a manageable level for the remaining circuit. Light indicator 20a is a light emitting diode which is energized to the proper voltage to indicate proper signal output. Indicator 20a can also be used to indicate that the monitor is in operation since it flickers at heart beat frequency of the patient. Inverting amplifier 20 is a low frequency amplifier which acts as a low power amplifier to distribute this signal to different circuits. Diode 21 allows minus potential only to flow to the succeeding circuitry. Control 22 serves as a bias regulator for diode 21 and permits minus polarity potential above the setting of control 22 to enter integrator 23 through switch 16 and also prevents leakage of the stored charge on storage capacitor 24. Integrator 23 consists of resistors 25, 25a and 25b; and storage capacitor 24. Capacitor 24 is charged negatively at every D.C. pulse produced by the action of the heart beat and breathing functions sensed by transducer 14. The sum of the pulsed voltages is related to the frequency of the pulses, e.g., the higher the pulse frequency the higher is the voltage stored in capacitor 24. Resistors 25, 25a and 25b limit the buildup of this voltage for any given time depending on the RC time constant of this circuit. The negative voltage generated in integrator 23 is fed to a low voltage detector 26. Detector 26 consists of an operational amplifier op-amp 27 of the 741 type which has been biased positive by variable resistor 28 to balance the output voltage of integrator 23 and produce a negative voltage output of op-amp 27 during a steady state frequency sensed, nominally 72 heart beats and 14 breathings per minute, by transducer 14. Resistors 29, 30 and 31 form a feedback signal network voltage divider and reduce the effect of a large offset current of op-amp 27. Low voltage detector 26 achieves gain higher than 5,000 and goes to an overload condition by a very small voltage input differential. This feature makes this circuit able to trigger relay 32 when there is a very small decrease in the absolute value of the negative voltage stored on capacitor 24 of integrator 23. The decrease in absolute negative voltage is due to the reduction of the frequency of the heart beat and breathing sensed by transducer 14. For instance, if the heart beat decreases to about 40 beats and the breathingg rate to about 8 beats per minute, the voltage integration resulting in capacitor 24 is reduced to a critical point of about $-2$ volts to trigger op-amp 27 from a minus potential output to full power plus potential output. Diode 33 allows flow of the positive potential to activate relay 32. Relay contacts 34 are activated by relay 32 and closes the circuit of terminal 35 and 36.

High gain inverting amplifier 37 is also fed by integrator 23. Variable resistor 38 and voltage divider resistors 39, 40 and 41 are chosen to maintain op-amp 42 at a plus bias potential of about +6 volts. If the heart beat and breathing functions increase, for instance, to about 110 and 25 respectively, the voltage integrated is increased and capacitor 24 obtains an absolute voltage in excess of the minus 6 volts which obtains under normal heart and respiration rates. For example with increased heart and respiration rates, the negative voltage on capacitor 24 may go to 7 or 8 volts. This action changes the bias voltage of op-amp 42 negatively which results in a positive output voltage. This triggering action causes a flow of positive current through diode 43 which activates relay 44. Switch 45 is activated by relay 44 and closes the circuit to terminals 35 and 36.

The circuitry of the two detectors 26 and 37 is similar except that in the case of the low voltage detector 26, the integrator voltage is applied to the positive input terminal of op-amp 27 from adjustable resistor 25a and in the high voltage detector 37 the integrator voltage from adjustable resistor 25b is applied to the negative input of op-amp 42. This difference in inputs is what produces the difference in function of these two otherwise similar circuits.

It should be noted that the circuit of FIG. 2 can be easily modified to accommodate positive voltages on storage capacitor 24. If diode 21 is reversed in polarity, positive voltage pulses would be applied to the integrator. The two detector circuits would then be modified to detect changes in the positive integrator voltage.

Also, other types of detectors could be used instead of those shown. One other type would be Schmitt trigger circuits. These circuits could be designed to trigger and actuate the alarms when the critical high and low voltages on integrator 23 obtain.

Figure 5:
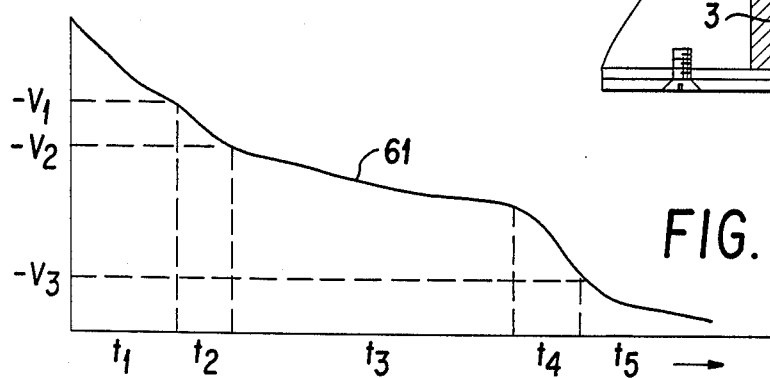
FIG. 5 is a curve indicating the various triggering voltage points to produce an alarm signal.

The values indicated in FIG. 2 for the capacitor and the resistors are only for explanatory purposes. These values can vary to conform with parameters chosen for the application of the device. The value of heart beat and breathing indicated are also to show some practical limits. For instance, adjusting the value of resistance 25b and 38 allows adjustment for triggering op-amp 42 at different frequency rates of heart and breathing actions which are above those of the patient at rest. Adjusting resistor 25a and 28 allows triggering points of op-amp 27 blow those of the patient at rest. FIG. 5 shows this application in a graph form.

The use of the very high gain non-inverting op-amp 27 and inverting op-amp 42 are electronic circuits that employ single op-amps to accomplish comparator functions combined with the triggering action to gate and amplify small signals. For instance, the change over from negative output to positive output of op-amp 27 and 42 is caused by a very small voltage differential on the input going from a positive to a less positive voltage of about 0.001. This small voltage differential is grated and amplified over 5,000 times at high slew triggering rates.

The negative current that goes through diode 21 is channeled through switches 46, 47 and 48 to integrator 23. Band pass filter 49 allows to pass only frequencies associated with the heart beat. These may be of the order of from 45 to 250 beats per minute. Band pass filter 50 allows to pass only frequencies associated with breathing. These may be of the order of 6 to 40 breathing cycles per minute. If switch 46 is closed and all other switches are open the two bandpass filters are out of the circuit and the output of diode 21 comprising both heart and respiration signals is applied to the integrator 23. Switches 47 and 51, when in the closed position and switch 46 in the open position, inserts respiration bandpass filter 49 between the diode 21 and integrator 23. Similarly if switches 48 and 52 are closed and switch 46 in the open position the heart bandpass filter 50 will be inserted between the diode 21 and the integrator, allowing only heart frequency signals to enter integrator circuit 23. This arrangement of switches allows the instrument to be used as a monitor for the combination of heart and breathing functions; heart function only or breathing function only. The control of these switches may be done from the outside of the alarm device. A visual monitor 53 which may consist of an oscilloscope or a strip chart recorder is connected by means of switch 53a to examine the wave shape produced by transducer 14 after being electronically processed. Visual monitor 53 can monitor the combined frequencies of the heart and breathing functions when switch 46 is conducting; the heart beat only when switches 48 and 52 are conducting; and the breathing only when switches 47 and 51 are conducting. Radio transmitter 54 can be connected to terminals 35 and 36 to transmit the alarm signals generated by amplifiers 27 and 42. In applications where the heart and breathing monitor is to be used in a private house, it may be more advantageous to eliminate from FIG. 2 the circuits associated with bandpass filters 49 and 50 and the visual monitor 53. These features may make the device unnecessarily more complex and expensive for such applications. However these features may be advisable for hospital applications.

The dc power supply needed to operate the monitor device has not been shown in the schematic diagram. This can be obtained from a conventional ac power source which has been rectified and the voltage adjusted to conform with the electronic component used. A battery power supply can also be used. In this manner the instrument which is placed on the bed where the patient rests is self-powered and eliminates power wiring to be attached to the bed structure. The battery can also be of the rechargeable type which can be recharged using house current without taking the battery out of the enclosure.

Figure 3:
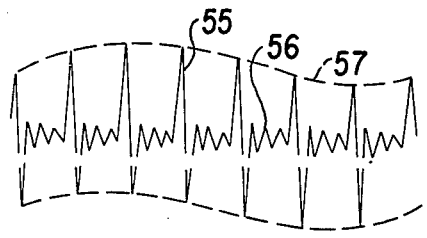
FIG. 3 is a schematic diagram of the unprocessed wave form produced by the heart and breathing rate transducer.

Turning to FIG. 3, it is a schematic of the unprocessed wave form from transducer 14. The high frequency wave form contains heart beat pulses 55 and ambient noises 56. In noises 56 there is also some signal that is related to the diagnostic condition of the heart function. However, this information is not the object of this invention, and is not discussed here. The breathing rate, low frequency 57 is shown by a dotted line with enclosed pulses 55.

Figure 4:
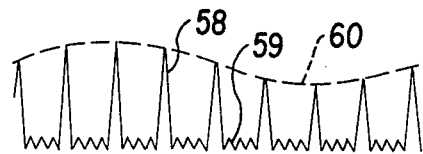
FIG. 4 is a schematic diagram of the wave shape of FIG. 3 after it has been rectified.

Turning to FIG. 4, it is a schematic of the wave shape shown in FIG. 3 after it has been rectified by diode 16. Rectified wave 58 corresponds to the unrectified wave 55. Rectified wave, shown in dotted lines 60 corresponds to the unrectified wave 57. Rectified wave 59 has a lower amplitude than the corresponding wave 56. This is a result of adjusting bias network 17 of FIG. 2 and setting the threshold of the rectified voltage to a suitable level.

Turning to FIG. 5, it is curve of the various triggering voltage points to produce an alarm signal for the circuit of FIG. 2. The negative voltage generated by integrator 23 is shown by curve 61. The curve 61 between the voltages $-V2$ and $-V3$ is generated by the voltage integrated by integrator 23 when transducer 14 is placed on the bed where the patient is resting. The patient's normal heart beat and breathing actions may fluctuate slightly during time t3 without causing a triggering action on amplifiers 27 and 42. This condition may last for an indefinite time if the patient's activity remains normal. The portion of the curve designated by $-V1$ and $-V2$ shows a period t2 during which time the absolute value of the voltage is declining due to the onset of apnea or bradycardia, or both. This condition slows the heart beat and the breathing period, resulting in a diminished voltage integration, as shown. If this condition continues for a period designated as t2, the triggering voltage $-V1$ is reached and amplifier 27 goes to the triggering mode producing a signal in terminals 35 and 36. The time interval t2 is normally adjusted to be 10 to 20 seconds. The adjustment of the time interval t2 is accomplished by adjusting the bias voltage of amplifier 27 with variable resistor 28. This adjustment is done by the operator of the alarm device in accordance with the needs of the patient. For instance, if the patient is a small child with suspected SID syndrome, it is advisable to adjust the variable resistor 28 so that the alarm triggers about 10 seconds after the attack of apnea. The knob operating resistor 28, now shown in the drawing, may be calibrated in units of time to guide the operator.

If the patient has an increase in the action of the heart beat or breathing, integrator 23 charges to a higher absolute voltage designated by $-V3$. At this point, amplifier 42 will go to the triggering mode and produce an alarm signal to terminal 35 and 36.

The alarm signal of the low activity and high activity of the patient are shown in FIG. 2 to terminate a the same point, i.e., terminals 35 and 36. However, these two signals, not shown in FIG. 2, may be separated if so desired. Amplifier 42 will also trigger an alarm signal if the high activity is caused by a physical movement of the patient which generates sufficient voltage in integrator 23. The curve portion designated as t4 indicates the time interval required for integrator 23 to reach the required triggering voltage. This time interval is also varied, similarly as t2, by the operator of the alarm device who can adjust variable resistor 38 which controls the bias triggering voltage of amplifier 42. The curve designated as t5 shows that the alarm stays on for an indefinite time until the alarm device is deactivated.

Figure 6:
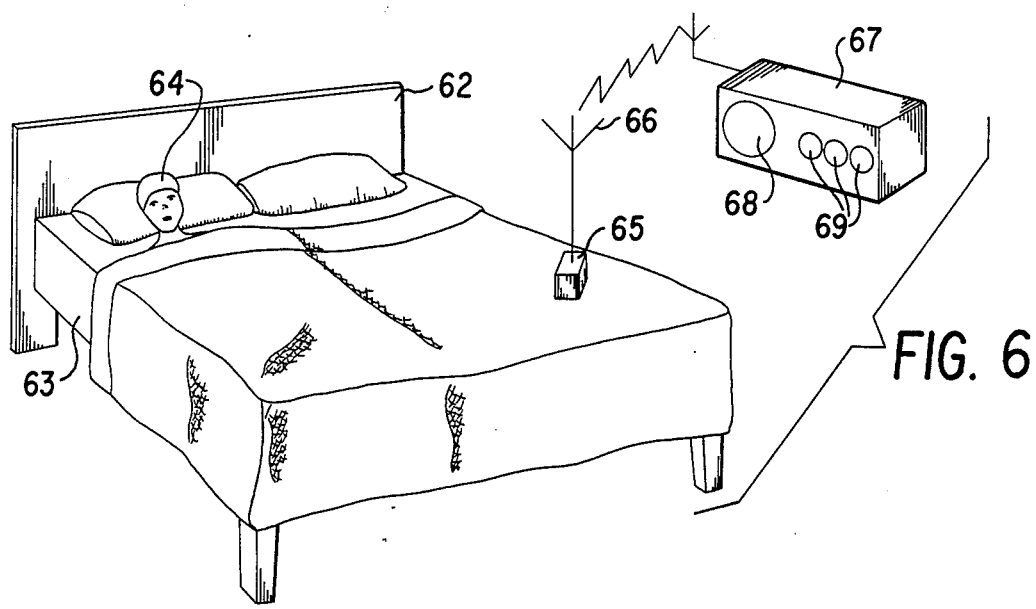
FIG. 6 is a representative view of the invention as may be used for a general application to monitor the heart and breathing functions of a patient.

Turning to FIG. 6, conventional bed 62 depicted as a conventional double size bed, supports a conventional mattress 63. Patient 64 rests on a portion of mattress 63. Heart and breathing monitor 65 is placed on one extreme portion of the mattress, which may be covered by a conventional sheet or blanket. Monitor 65 contains the electronics of FIG. 2 as well as the transducer of FIG. 1 to detect apnea and bradycardia, excessive heart and breathing rates and high activity physical movements that can cause damage to the patient. Radio transmitter 54 transmits, through antenna 66, an alarm signal when the above conditions are sensed by transducer 14 located within monitor 65. Radio receiver 67 receives the alarm signal and produces an audible sound which is generated in speaker 68. Electrical lights 69 may be made to flash to give a visual display that the alarm has been tripped.. The number of light indicators can vary depending on the application of the instrument. Using conventional electrical circuitry, not shown in FIG. 6, radio transmitter 54 can transmit a coded signal identifying the location of the bed. This coded information may be decoded by conventional circuitry, not shown in FIG. 6, in receiver 67 and the proper light will flash to indicate the location of the patient requiring attention. This feature can be used in locations where more than one patient is being monitored an the radio receiver is located at a central point.

The double size conventional bed 62 has been depicted to indicate the large area of sensitivity of monitor 65. It further depicts that monitor 65 does not require body coupling with the patient in order to sense the heart and breathing functions. Therefore, it can operate within large areas of mattresses. Mattress areas of conventional double and single bed sizes, hospital beds, baby cribs, incubator cribs and the like are within the scope of this invention and monitor device.

While the invention has been shown and described with reference to a specific embodiment and electronic processing, it is not limited to the configuration of electronic circuitry and components used for the specific circuits shown in the preferred embodiment, since other alternate electronic circuits and mechanical construction can produce satisfactory results. It should be obvious to those skilled in the state-of-the-art that various changes and modifications can be made to this specific embodiment without departing from the spirit and scope of this invention.

I claim:

1. An alarm device for detecting abnormal heartbeat and respiration of a person resting on a mattress in a bed, comprising
    means for detecting vertical movements of the upper surface of the mattress at a location on said mattress remote from said person, said mattress movements occurring at sub-sonic frequencies and being caused by movements of the person's body which result from the heartbeat and respiration of the person, said detecting means comprising mechanical/electrical transducer means adapted to rest under the influence of gravity on and in contact with said upper surface for converting said movements of said upper surface to an electrical signal having a frequency dependent upon the heart rate of the person and an envelope dependent upon said respiration; and
    means responsive to said electrical signal for indicating when said heart rate and/or said respiration is outside of a preselected "normal" range whereby the alarm can be placed on top of a mattress supporting a person to pick up vertical vibrations of the mattress due to the person's heart and respiratory motions and issue an alarm if the person's heart and/or respiration rate is outside of a preselected range.

2. The alarm device of claim 1 wherein said transducer comprises a case adapted to rest on said bed remote from said person, a cup-shaped pole piece within said case with a permanent magnet centrally mounted within said pole piece, whereby a radical magnetic field is set up within an air gap between said permanent magnet and the inside of said pole piece, a movable coil mounted on a form, said form being suspended within in said air gap, one end of said form being attached to a flexible diaphragm, the other end of said form being unattached, and an elongated sealed chamber extending above said diaphragm, said diaphragm forming the base of said chamber, said chamber being filled with a liquid or specific gravity greater than one.

3. An alarm device according to claim 1, including means connected to said transducer for band-pass filtering high and low frequency signals corresponding to said heartbeat and said respiration, respectively, and switch means for coupling (a) said heartbeat signals, or (b) said respiration signals, or (c) the combination of said heartbeat and respiration signals to said indicating means.

4. The alarm device of claim 3 wherein said transducer comprises a case adapted to rest on said bed remote from said person, a cup-shaped pole piece within said case with a permanent magnet centrally mounted within said pole piece, whereby a radical magnetic field is set up within an air gap between said permanent magnet and the inside of said pole piece, a movable coil mounted on a form, said form being suspended within said air gap, one end of said form being attached to a flexible diaphragm, the other end of said form being unattached, and an elongated sealed chamber extending above said diaphragm, said diaphragm forming the base of said chamber, said chamber being filled with a liquid of specific gravity greater than one.

5. The method of detecting abnormal heart rate and respiration of a patient resting on a mattress in a bed, comprising the steps of placing a transducer on and in contact with the upper surface of the mattress at a location spaced away from the patient,
    detecting vertical movements of the upper surface of the mattress at said location, said mattress movements occurring at sub-sonic frequencies and being caused by movements of the patient's body resulting from the heart rate and respiration of the patient, by using the transducer to generate an electrical signal having a frequency dependent upon the heart rate and an envelope dependent upon respiration, and
    providing an alarm when said electrical signal indicates that the heart rate and/or respiration is outside of a preselected normal range.

* * * * *